US00PP23718P3

(12) United States Plant Patent
Bradford

(10) Patent No.: US PP23,718 P3
(45) Date of Patent: Jul. 9, 2013

(54) INTERSPECIFIC TREE NAMED 'BLACKRED VI'

(50) Latin Name: ***Prunus* sp.**
Varietal Denomination: Blackred VI

(76) Inventor: Lowell Glen Bradford, Le Grand, CA (US)

( * ) Notice: Subject to any disclaimer, the term of this patent is extended or adjusted under 35 U.S.C. 154(b) by 62 days.

(21) Appl. No.: 13/374,020

(22) Filed: Dec. 8, 2011

(65) Prior Publication Data

US 2013/0152242 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP19,576 P2 12/2008 Bradford

*Primary Examiner* — Annette Para

(57) ABSTRACT

The present invention relates to an interspecific tree and more particularly to a new and distinct variety broadly characterized by a medium size, vigorous, hardy, and productive tree. Being self-unfruitful, the present variety requires cross pollination from an apricot, interspecific, or plum that blooms during the early season. The present variety produces a very heavy bloom with an abundance of pollen to entice good bee activity to facilitate pollination. The fruit matures under the ecological conditions described during late June, with the first picking on Jun. 27, 2011. The fruit is uniformly medium to large in size, very dark red in skin color, clingstone in type, oblate in shape, full red in flesh color, firm in texture, and very good in flavor.

1 Drawing Sheet

Botanical classification: *Prunus* sp.
Varietal denomination: 'BLACKRED VI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Blackred VI'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2003 one such house containing an unpatented red plum, code named '19P442', was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "H8". They were grown as seedlings on their own root in my greenhouse and upon reaching dormancy transplanted to a cultivated area of my experimental orchard located near Le Grand, Calif. in Merced County (San Joaquin Valley). During the summer of 2005 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '19P442' plum (unpatented) by being self-unfruitful and by producing fruit that is dark red to purple in skin color, red in flesh color, juicy, clingstone in type, and that matures in late June, but is distinguished therefrom by producing fruit that is sweeter in flavor, larger in size, and firmer in texture.

The present variety is most similar to 'BLACKRED V' interspecific tree (U.S. Plant Pat. No. 19,576) by being self-unfruitful and by producing fruit that is very dark red to blackish red in skin color, full red in flesh color, juicy, and firm, but is distinguished therefrom by producing fruit that is oblate instead of globose in shape, that is somewhat larger in size, and that matures about seven days earlier.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the early season. The present variety produces a very heavy bloom with an abundance of pollen to entice good bee activity to facilitate pollination. The fruit matures under the ecological conditions described during late June, with the first picking on Jun. 27, 2011. The fruit is uniformly medium to large in size, very dark red in skin color, clingstone in type, oblate in shape, full red in flesh color, firm in texture, and very good in flavor.

DRAWING

The accompanying photograph consists of four whole fruits positioned to display the characteristics of the skin color and form, one half of a fruit divided transversely to the suture plane to reveal the flesh and stone, a freshly cleaned stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 3, 2011, on the original tree during its eighth growing season. The flower and bud descriptions were developed during the previous blooming season. All major color code designations are by reference to the Inter-Society Color Council, National Bureau of Standards. Common color names are also used.

PARENTAGE

Seed parent: '19P442' plum (unpatented).
Pollen parent: Unknown.

TREE

Size: Medium, reaching and maintaining a height of 12' [3.66 m.] and a spread of 6' [1.83 m.] after eight growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable early seasonal blooming apricot, interspecific, or plum, such as 'Blackred VIII' interspecific tree (U.S. Plant Pat. No. 20,863).

Bearing: Regular bearer with no crop failures yet observed, weather dependent.

Trunk:

- *Size.*—Medium, reaching a maximum diameter of 5" [127 mm.] after the eighth growing season.
- *Texture.*—Medium shaggy.
- *Bark color.*—A Grayish brown [61. gy.Br] and Dark brown [59. d.Br] variegation with Light brown [57. l.Br] crevices present.
- *Lenticels.*—Approximate Number Per Square Inch: 10. Color: Light orange [52. l.O]. Size: ¼" [6.4 mm.] to 7/16" [11.1 mm.]. Shape: Eye-shaped, elongated.

Branches:

- *Size.*—Main scaffold diameter is 3" [76.2 mm.] measured 12" above the crotch, limb diameter is 1¾" [44.5 mm.] measured 12" above the first fork.
- *Texture.*—Smooth on first year wood, increasing roughness with age.
- *Color.*—1st Year Wood Topside: Grayish red [19. gy.R]. 1st Year Wood Underside: Brilliant yellow green [116. brill.YG]. 2nd Year Wood: Strong brown [55. s.Br] with Strong yellow green [117. s.YG] permeating through from underneath.
- *Lenticels.*—Number Per Square Inch: About 60 on second year wood. Color: Deep orange yellow [69. deep OY]. Size: 1/64" [0.4 mm.] to 1/16" [1.6 mm.]. Shape: Elongated, eye-shaped.

Leaves:

- *Size.*—Large. Average Length: 4¼" [108 mm.]. Average width: 2⅛" [54 mm.].
- *Arrangement.*—Alternate.
- *Thickness.*—Medium.
- *Form.*—Ovate.
- *Apex.*—Acuminate.
- *Base.*—Some obtuse and some acute.
- *Surface.*—Smooth.
- *Color.*—Dorsal Surface: Grayish olive green [127. gy.OlG]. Ventral Surface: Moderate olive green [125. m.OlG].
- *Margin.*—Finely serrate.
- *Venation.*—Pinnately net veined.
- *Petiole.*—Average Length: ½" [12.7 mm.]. Average Thickness: 1/16" [1.6 mm.]. Color: Moderate yellow green [120. m.YG].
- *Stipules.*—Number: 2 per leaf, up to 6 per growing tip. Average Length: ¼" [6.4 mm.]. Color: Very light yellowish green [134. v.l.yG] becoming Strong yellowish green [131. s.yG] with age.
- *Glands.*—Number: Mostly 3 to 4 per leaf. Position: Mostly alternate, positioned on the petiole and the base of the leaf blade. Size: Medium. Form: Globose. Color: Brilliant yellowish green [130. brill.yG] acquiring a Moderate yellow green [120. m.YG] center with age.
- *Leaf buds.*—Pointed, medium.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.

- *Average flower diameter.*—1" [25.4 mm.].
- *Number of petals.*—Five, no double blossoms observed.
- *Petal shape.*—Oval to circular.
- *Petal margin.*—Entire, somewhat wavy with notches typical.
- *Average petal diameter.*—½" [12.7 mm.].
- *Average petal length.*—9/16" [14.3 mm.].
- *Petal apex.*—Rounded.
- *Petal base.*—Obtuse.
- *Petal color.*—White [263. White] on both sides.

*Anther color.*—Deep orange yellow [69. deep OY].
*Stigma color.*—Brilliant greenish yellow [98. brill.gY].
*Sepal color.*—Light yellow green [119. l.YG] on the outer surface.
*Sepal length.*—3/16" [4.8 mm.].
*Sepal width.*—5/32" [4.0 mm.].
*Sepal apex.*—Rounded to elliptical to match the width and length.
*Sepal margin.*—Fairly smooth to the naked eye, slightly serrate toward the apex when magnified.
*Average pistil length.*—11/16" [17.5 mm.].
*Average stamen length.*—½" [12.7 mm.].
*Fragrance.*—Moderate.
*Pollen production.*—Abundant, bee enticing.
*Bloom density.*—Heavy.
*Number per cluster.*—2 to 10, average 5.
*Blooming period.*—Early, two days after 'Yummy® gem' plum (U.S. Plant Pat. No. 15,809).
*Onset of bloom.*—One percent on Feb. 18, 2011.
*Date of full bloom.*—Mar. 2, 2011.
*Duration of bloom.*—One to two weeks, dependent on ambient temperature.

FRUIT

Maturity when described: Firm ripe, Jul. 3, 2011.
Date of first picking: Jun. 27, 2011.
Date of last picking: Jul. 10, 2011.
Size: Uniform, medium to large.
*Average diameter axially.*—2⅛" [54 mm.].
*Average diameter across cheek plane.*—2 9/16" [65.1 mm.].
*Average diameter across suture plane.*—2⅝" [66.7 mm.].
*Typical weight.*—4.9 ounces [138.9 grams].
Form: Uniform, oblate, symmetrical.
*Longitudinal section form.*—Oblate.
*Transverse section through axial diameter.*—Round.
Suture: An inconspicuous line in a shallow groove extending from the base to the apex.
Ventral surface: Rounded, slightly lipped toward the base.
Lips: Mostly equal.
Cavity: Flaring, circular, stem markings generally not present.
*Depth.*—⅜" [9.5 mm.].
*Breadth.*—¾" [19.1 mm.].
Base: Truncate, slightly cordate if viewed parallel to the suture.
Apex: Rounded to truncate.
Pistil point: An inconspicuous Pale yellow green [121. p.YG] dot.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Slight.
*Tendency to crack.*—Non observed in dry season.
*Color.*—Very dark red [17. v.d.R] over a Very deep red [14. v.deep R] background with Pale yellow [89. p.Y] freckles throughout.
*Bloom.*—Abundant.
Flesh:
*Color.*—Deep red [13. deep R] with a Dark red [16. d.R] ring just under the skin.
*Surface of pit cavity.*—Covered with Deep red [13. deep R] broken fibers when twisted from the stone.
*Amygdalin.*—Scarce.
*Juice.*—Moderate, rich.
*Texture.*—Firm, tough, crisp.
*Fibers.*—Few, fine, tender.
*Ripens.*—Slightl1y earlier toward the apex.
*Flavor.*—A tasty blend of acid and sugar, typically 16 to 18 brix.
*Aroma.*—Slight.
*Eating quality.*—Very good.

STONE

Type: Clingstone.
Form: Oval.
Hilum: Narrow to flat.
Base: Flat.
Apex: Acute.
Sides: Equal.
Surface: Regularly furrowed throughout with a few irregular ridges on both sides of the dorsal fin.
External color of stone: Yellow white [92. yWhite].
Pit wall color when cracked: Pale yellow [89. p.Y].
Cavity surface color: Pale yellow [89. p.Y].
Average pit wall thickness: ⅛" [3.2 mm.].
Average width: 11/16" [17.5 mm.].
Average length: 13/16" [20.6 mm.].
Average breadth: ⅜" [9.5 mm.].
Tendency to split: None observed.
Kernel:
*Form.*—Oval.
*Skin color.*—Light yellow green [119. l.YG] when first removed.
*Pellicle color.*—Brilliant yellow green [116. brill.YG].
*Vein color.*—Brilliant yellow green [116. brill.YG].
*Taste.*—Slightly bitter.
*Viable.*—Yes.
*Average width.*—⅜" [9.5 mm.].
*Average length.*—½" [12.7 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'BLACKRED V' interspecific tree (U.S. Plant Pat. No. 19,576) by being self-unfruitful and by producing fruit that is very dark red to blackish red in skin color, full red in flesh color, juicy, and firm, but is distinguished therefrom by producing fruit that is oblate instead of globose in shape, that is somewhat larger in size, and that matures about seven days earlier.

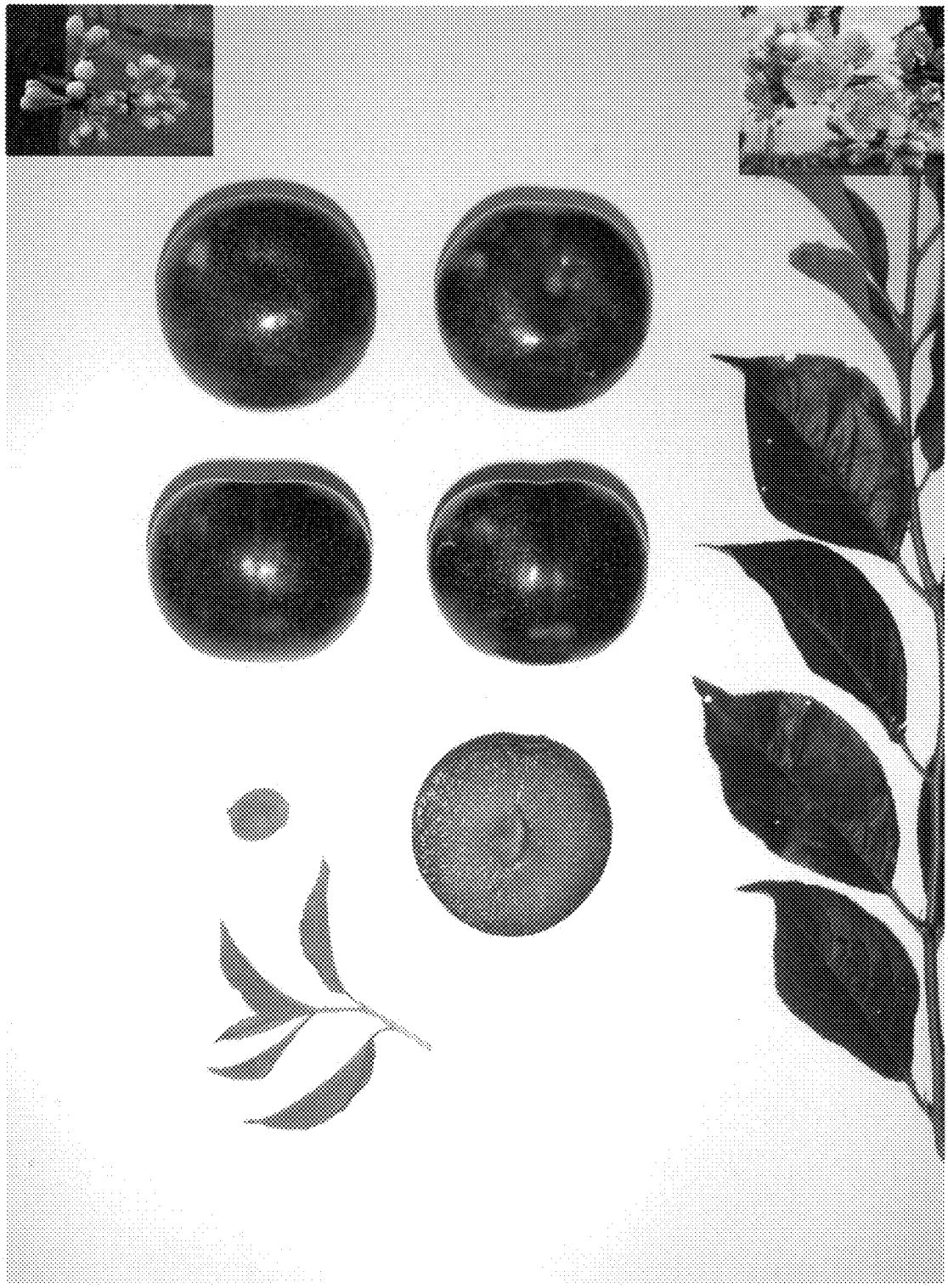

* * * * *